(12) United States Patent
Caillat et al.

(10) Patent No.: US 6,803,228 B1
(45) Date of Patent: Oct. 12, 2004

(54) METHOD FOR MAKING A BIOCHIP AND BIOCHIP

(75) Inventors: Patrice Caillat, Echirolles (FR); Charles Rosilio, Gif sur Yvette (FR)

(73) Assignee: Commissariart A L'Energie Atomique, Paris (FR)

( * ) Notice: Subject to any disclaimer, the term of this patent is extended or adjusted under 35 U.S.C. 154(b) by 0 days.

(21) Appl. No.: 09/868,043

(22) PCT Filed: Dec. 15, 1999

(86) PCT No.: PCT/FR99/03141

§ 371 (c)(1),
(2), (4) Date: Jun. 14, 2001

(87) PCT Pub. No.: WO00/36145

PCT Pub. Date: Jun. 22, 2000

(30) Foreign Application Priority Data

Dec. 16, 1998  (FR) ............................................. 98 15883

(51) Int. Cl.[7] ........................... C12Q 1/68; C12P 19/34; C12M 1/34; C07H 21/02; C07H 21/04
(52) U.S. Cl. ............................ 435/287.2; 435/5; 435/6; 435/7.1; 435/91.1; 435/91.2; 536/22.1; 536/23.1; 536/24.3; 536/24.31; 536/24.32; 536/24.33; 422/50; 422/68; 422/76; 422/82.07; 204/165; 205/158
(58) Field of Search ..................... 435/6, 70.1, 320.1, 435/5, 7.1; 530/350; 536/23.4, 25.3; 205/158; 204/165; 422/50, 68, 76, 82.07

(56) References Cited

U.S. PATENT DOCUMENTS

| | | | |
|---|---|---|---|
| 5,151,162 A | * | 9/1992 | Muller ........................ 294/131 |
| 5,653,939 A | | 8/1997 | Hollis et al. .................. 422/50 |
| 5,810,989 A | | 9/1998 | Krihak et al. ................. 205/91 |
| 5,837,859 A | | 11/1998 | Teoule et al. ............... 536/25.3 |
| 6,312,896 B1 | * | 11/2001 | Heroux ........................... 435/6 |
| 6,316,229 B1 | * | 11/2001 | Lizardi ....................... 435/91.1 |
| 6,682,936 B2 | * | 1/2004 | Kovacs ........................ 436/149 |
| 6,683,189 B1 | * | 1/2004 | Deryan et al. ........... 548/312.7 |

FOREIGN PATENT DOCUMENTS

| | | |
|---|---|---|
| EP | 0 038 244 | 10/1981 |
| EP | 0 229 993 | 7/1987 |
| EP | 0 588 721 | 3/1994 |
| EP | 0 659 794 | 6/1995 |

OTHER PUBLICATIONS

T. Livache, et al., Nucleid Acids Research, vol. 22, No. 15, pp. 2915–2921, "Preparation of a DNA Matrix Via an Electrochemically Directed Copolymerization of Pyrrole and Oligonucleotides Bearing a Pyrrole Group", 1994.

(List continued on next page.)

*Primary Examiner*—Jeffrey Siew
(74) *Attorney, Agent, or Firm*—Oblon, Spivak, McClelland, Maier & Neustadt, P.C.

(57) ABSTRACT

The present invention relates to a method to produce a biochip and to a biochip, said biochip being composed particularly of biological probes grafted onto a conductive polymer.

The method according to the invention comprises the following steps:
a) structuring of a substrate so as to obtain on said substrate microtroughs comprising in their base a layer of a material capable of initiating and promoting the adhesion onto said layer of a film of a pyrrole and functionalised pyrrole copolymer by electropolymerisation,
b) collective electropolymerisation, so as to form an electropolymerised film of a pyrrole and functionalised pyrrole copolymer on the base of said microtroughs,
c) direct or indirect fixation of functionalised oligonucleotides by microdeposition or a liquid jet printing technique.

29 Claims, 3 Drawing Sheets

OTHER PUBLICATIONS

T. Livache, et al., Biosensors and Bioelectronics, vol. 13, pp. 629–634, "Electroconducting Polymers for the Construction of DNA or Peptide Arrays on Silicon Chips", 1998.

T. Livachi, et al., Analytical Biochemistry, vol. 255, Article No. AB972462, pp. 188–194, "Polypyrrole DNA Chip on a Silicon Device: Example of Hepatitis C Virus Genotyping", 1998.

R.A. Simon, et al., Journal of the American Chemical Society, vol. 104, No. 7, pp. 2031–2034, "Synthesis and Characterization of a New Surface Derivatizing Reagent to Promote the Adhesion of Polypyrrole Films to n–Type Silicon Photoanodes: N–(3–(Trimethoxysilyl)Propyl) Pyrrole", 1982.

A. Guiseppi–Elie, et al., Langmuir, vol. 11, No. 5, pp. 1768–1776 "Specific Immobilization of Electropolymerized Polypyrrole Thin Films onto Interdigitated Microsensor Electrode Arrays", 1995.

M. Nishizawa, et al., Journal of Physical Chemistry, vol. 95, No. 23, pp. 9042–9044, "Electrochemical Preparation of Ultrathin Polypyrrole Film at Microarray Electrodes", 1991.

G. Bidan, et al., Synthetic Metals, vol. 102, pp. 1363–1365, "Conducting Polymers as a Link Between Biomolecules and Microelectronics", 1999.

I. Jirkovsky, et al., Synthesis, pp. 481–483, "A Facile, Large–Scale Preparation of 1H–Pyrrole–1–Ethanamine and Syntheses of Substituted Pyrrolo[1,2–a]Pyrazines and Hydro Derivatives Thereof", Jun. 1981.

* cited by examiner

METHOD FOR MAKING A BIOCHIP AND BIOCHIP

FIELD OF THE INVENTION

The present invention relates to a method to produce a biochip and to a biochip, said biochip being composed particularly of biological probes grafted onto a conductive polymer.

Biological analysis devices, for example DNA chips, represent high-performance tools for the parallel analysis of a large number of genes or DNA or RNA sequences. Their operating principle is based on the hybridisation or pairing property of two strands of complementary sequences in order to reconstitute the DNA double helix. To do this, oligonucleotide probes of a known sequence, immobilised on a support substrate, are placed in the presence of targets extracted from a biological specimen under analysis, and labelled using fluorescent markers.

The hybridisation is then identified and the sequence detected by analysing the surface of the chip with a suitable marker for example to detect the sequence by fluorescence.

Very different technologies have been used to produce these probe matrices. Various immobilisation or grafting techniques of probes onto different substrates have been the subject of significant studies and industrial developments.

1. State of the Related Art

There are essentially three chemical probe addressing methods which represent different approaches to the production and use of probes for different fields of application. They consist of photochemical addressing, mechanical addressing, for example by micropipetting using a dispersion robot, and electrochemical addressing.

For example, electrochemical addressing may be used for oligonucleotide probes. To do this, individually addressed electrode matrices are produced on a glass substrate.

The biological probe immobilisation principle is based on the electropolymerisation deposition of a copolymer of pyrrole and pyrrole substituted by an oligonucleotide (Py-ODN), comprising an oligonucleotide grafted onto a pyrrole nucleus either directly, or indirectly by means of a spacer.

In order to develop massively parallel biological analysis systems, with a high capacity or active site density, it is necessary to be able to address a large number of probes.

Methods using electrochemical addressing require both a large electrode and connection matrix and a multiplexer to index each of the chip's sites electrically. In addition, in these methods, it is necessary to carry out electropolymerisation by immersing the entire chip successively in solutions of each of the Py-ODNs contained in the cell. Therefore, these methods are limited to low-density chips, i.e. comprising approximately one hundred probes, for limited and specific applications.

Other methods have been described in the prior art, advantageously replacing individual electrical addressing by mechanical addressing. However, a disadvantage remains, that of carrying out electropolymerisations in microtroughs, with a solution volume of the order of one nanolitre, for which it is necessary to delay evaporation after micropipetting of all the probes on the insert so that electropolymerisation may take place.

2. Description of the Invention

The aim of the present invention is specifically to solve the above-mentioned problems by providing a method to produce a biochip composed particularly of biological probes grafted onto a conductive polymer, said method particularly offering the advantage of only requiring the use of a single solution of a mixture of suitable proportions of pyrrole and substituted pyrrole (Py and Py-R-F or F and a reactive chemical function and R is an aliphatic or aromatic spacer group) for a single collective electrodeposition on all the microtroughs.

The method according to the invention is characterised in that it comprises the following steps:

a) structuring of a substrate so as to obtain on said substrate microtroughs comprising in their base a layer of a material capable of initiating and promoting the adhesion onto said layer of a film of a pyrrole and functionalised pyrrole copolymer by electropolymerisation, b) collective electropolymerisation, so as to form an electropolymerised film of a pyrrole and functionalised pyrrole copolymer on the base of said microtroughs, on the layer of said material, using a pyrrole and functionalised pyrrole solution, in the presence of suitable chemical reagents for said electropolymerisation, c) direct or indirect fixation of a biological probe onto the functionalised pyrrole, by injecting a biological probe solution, either in one or more microtroughs in the presence of chemical reagents required for the direct or indirect fixation of this biological probe onto the functionalised pyrrole.

According to the invention, the layer of material capable of initiating and promoting the adhesion of a film of a pyrrole and functionalised pyrrole copolymer by electropolymerisation onto said layer may be a metallic layer, step a) mentioned above possibly comprising a deposition step of said metallic layer onto the substrate, and a deposition step of a layer of resin or polymer onto the metallic layer and development or engraving of said layer so as to form microtroughs, wherein the base is composed at least partly of the metallic layer.

According to the invention, the metallic layer may be, for example, a layer of gold, a layer of copper or silver or aluminium.

According to the invention, the substrate may be for example a silicon insert, a glass insert or a flexible plastic support if required.

According to another embodiment of the present invention, the step a) may also comprise a treatment step of the gold layer at the base of the microtroughs in the presence of a functionalised pyrrole for example with a thiol group so as to form a monolayer of pyrrole onto said metallic layer, for example on said gold layer, at the base of said microtroughs. This monolayer is capable of initiating and promoting the adhesion of a polypyrrole film by electropolymerisation as demonstrated by R. Simon et al., J. Am. Chem. Soc., 1982, 104, 2031). This is a self-assembled monolayer SAM of a functionalised pyrrole for its adhesion onto the base of the microtroughs.

According to the invention, the functionalised pyrrole may be a pyrrole which comprises a chemical group enabling its fixation by covalent bonding with the metallic layer, and/or with the biological probe. In the case of its fixation to the metallic layer, for example to the gold layer, a functionalised pyrrole with a thiol or disulphide group may also be used.

For example, the functionalised pyrrole with a thiol group may have the following chemical formula:

wherein n may have a value ranging from 1 to 10, for example n may be equal to 6.

For a metallic aluminium probe, a functionalised pyrrole with a —COOH group may be chosen.

According to another embodiment of the present invention, the substrate may be a silicon insert and the layer capable of initiating and promoting the adhesion onto said layer of a polypyrrole film by electropolymerisation may be a layer of silane comprising an alignment of pyrrole sites. Step a) of the method according to the present invention may in this case comprise a deposition step of a layer of resin on the silicon insert, said silicon insert being coated with an $SiO_2$ film, and engraving of said resin layer so as to form the microtroughs wherein the base is composed at least partly of the $SiO_2$ film; and a microtrough treatment step by means of a functionalised silanisation agent with a pyrrole so as to fix, on the $SiO_2$ film, in the base of the microtroughs, the silane layer comprising an alignment of pyrrole sites.

According to the invention, the silanisation agent may be chosen in a group comprising N-(3-(trimethoxy silyl) propyl) pyrrole, or any other functionalised pyrrole with an —$SiCl_3$ or —$Si(OMe)_3$ group. The $SiO_2$ film may be a natural $SiO_2$ film present on silicon inserts.

According to the invention, irrespective of the embodiment, the resin may be a photosensitive resin, wherein masking, insolation and development are used to form the microtroughs.

According to the invention, the collective electropolymerisation in step b) of the method may be carried out for example by immersing the structured substrate obtained in step a) mentioned above in an electrolytic bath comprising a solution of pyrrole, functionalised pyrrole, and suitable chemical reagents for electropolymerisation, in the presence of a counter-electrode to the working electrode which is immersed in the electrolytic bath and is independent of the structured substrate.

According to the invention, in this step b), the functionalised pyrrole may be a pyrrole comprising a group chosen in a set comprising an $NH_2$ group, a thiol group a succinimide ester group, a trimethoxy silyl group, a carboxyl, aldehyde and isothiocyanate group.

According to the invention, the functionalised pyrrole by electropolymerisation may for example be chosen from one of the following compounds:

PYRROLE

N-ETHYLAMINE PYRROLE

N(3-(TRIMETHOXY SILYL) PROPYL) PYRROLE

Functionalised PYRROLE with a thiol

Functionalised PYRROLE in 3' by a succinimydyl ester.

According to the invention, the electrolytic bath may be a mixture of pyrrole and functionalised pyrrole in suitable proportions to form a film comprising a required number of units of functionalised pyrrole. In this way, the method according to the invention makes it possible to choose the number of biological probes per microtrough, since according to this method, the biological probes are fixed, either directly or indirectly on said functionalised pyrroles.

The next step c) of the method according to the invention consists of a direct or indirect fixation of a biological probe onto the functionalised pyrrole.

According to the invention, when the fixation of the biological probe is indirect, the step c) of the method according to the invention may also comprise, before the fixation of the biological probe, a collective fixation of a cross-linking agent on the functionalised pyrrole, in the presence of suitable chemical reagents, said cross-linking agent comprising a first function enabling its fixation onto the functionalised pyrrole, and a second function enabling the fixation of the biological probe on said cross-linking agent.

According to the invention, the cross-linking agent may for example be a bi-functional cross-linking agent.

The cross-linking agent may for example comprise an N-hydroxysuccinimide ester function and a maleimide function.

According to the invention, the cross-linking agent may for example be chosen from one of the following compounds;

N-hydroxysuccinimide ester maleic function
SMPB
succinimidyl 4-(p-maleimidophenyl)butyrate

GMBS
N-maleimidobutyryloxy succinimide ester,
a dialdehyde of the type

GLUTARALDEHYDE,
a diisothiocyanate of the type 1,4-PHENYLENE DIISOTHIOCYANATE,

SUCCINIC ANHYDRIDE OR SUCCINIC ACID
or a derivative of these compounds.

All the bi-functional cross-linking agents mentioned above are suitable for functionalised polypyrroles with the —$CH_2$—$CH_2$—$NH_2$ group in position 1 on nitrogen. However, electropolymerisation with a functionalised pyrrole with other groups is also possible. For example, Py-$CH_2$—$CH_2$—$NH_2$, Py-SH, Py-succinimidyl ester (in 3), Py-hydrazine with a substitution in 1 on nitrogen or in 3 on the pyrrole cycle, making it possible to immobilise the oligonucleotides, either directly or by means of a cross-linking agent, for example a bi-functional agent.

The following cross-linking agents may therefore be used in the method according the present invention:

a) a glutaraldehyde type dialdehyde, which may react on the $NH_2$ function of the polypyrrole film (collective step) and then on the $NH_2$ function of an oligonucleotide terminated for example by a phosphate comprising an amino group, by an individual step in the microtroughs;

b) a diisothiocyanate which may also react on the amine function of the functionalised polypyrrole at one end (collective step) and then on an amine function of an oligonucleotide terminated by a phosphate with a functionalised spacer group with $NH_2$;

c) a succinic anhydride, which for each opening, comprises two acid functions capable of reacting on the $NH_2$ groups of the polypyrrole and on the $NH_2$ groups of a functionalised oligonucleotide with $NH_2$.

According to the invention, the biological probe which will be the source of the specificity of the manufactured biochip, may be chosen for example from an oligonucleotide, a DNA, an RNA, a peptide, a glucide, a lipid, a protein, an antibody, an antigen.

According to the invention, the biological probe is preferentially functionalised to be able to be fixed either directly or indirectly on the functionalised pyrrole. The purpose of this functionalisation is to fix on the biological probe a chemical group capable of forming a covalent bond between the biological probe and the functionalised pyrrole.

It may be for example functionalised with a thiol group, with an $NH_2$ group, aldehyde, a —COOH group or an acid phosphate group.

For example, when the biological probe is an oligonucleotide, it may be functionalised with a thiol group SH. The functionalised oligonucleotides with S—H may be prepared according to a known procedure, for example at the end of an automated oligonucleotide synthesis.

If it is easier to use functionalised oligonucleotides with $NH_2$, it is possible for example to synthesise a functionalised pyrrole with an S—H for copolymerisation, to use for example SMPB with its two specific functions and immobilise the functionalised oligonucleotides with $NH_2$ by covalent bonding with the succinamide function of this cross-linking agent.

In the case of oligonucleotides terminated in 3' by an N-methyl uridine nucleotide, an oxidation reaction on this function makes it possible to obtain a functionalised oligonucleotide with an aldehyde function, capable of reacting directly, i.e. for example without the bi-functional agent on the functionalised polypyrrole with $NH_2$.

To functionalise an oligonucleotide with an $NH_2$ function, one of the methods that may be used according to the method of the present invention may consist of coupling the oligonucleotide and commercially available N-trifluoroacetyl-6 amino hexyl-2 cyanoethyl NN'-diisopropyl phosphoramidite.

In addition, a functionalised oligonucleotide with $NH_2$ may for example be converted into an oligonucleotide terminated by a thiol with a reaction with dithiobis (succinimidylpropionate).

The functionalised probe oligonucleotides may for example be taken up by micropipetting in microwells and injected into the microtroughs for example by means of a dispensing microrobot or by jet printing. These devices are well-known to those skilled in the art.

The method according to the present invention makes it possible advantageously to choose the number of probes per active site, i.e. per microtrough by adjusting the proportion of functionalised pyrrole with reference to the pyrrole.

The required probe density may be monitored for example by fixing oligonucleotides labelled at the chain ends by a biotin and using streptavidine-Cy3 detection by a surface analysis of the chip using conventional fluorescence detection methods.

Another advantage of the method according to the invention lies in the fact that both collective operations, electropolymerisation and fixation of the cross-linking agent if applicable, may be carried out in batches on a large number of inserts in parallel.

The inserts having undergone step a) and b) of the method according to the invention are also referred to as "blank biochips". They are ready to undergo the direct or indirect fixation step of a biological probe, for example of an oligonucleotide according to the present invention.

In this way, the method according to the invention makes it possible for example to produce an oligonucleotide chip comprising in this order:

- a silicon substrate coated in silica, and a functionalised silane layer with pyrrole, or
- a gold layer or a silane layer comprising pyrrole sites, or
- a gold layer with or without an electropolymerisation promotion and adherence layer (based on a functionalised pyrrole with an —SH thiol), or
- an aluminium layer with a functionalised pyrrole with a —COOH,
- and a resin layer wherein microtroughs have been produced such that the base of said microtroughs is composed at least partly of the gold layer or the silane layer comprising pyrrole sites,
- and a layer of pyrrole and functionalised pyrrole copolymer, fixed on the gold layer or the silane layer comprising pyrrole sites forming the base of said microtroughs, the functionalised pyrrole being bound to a bi-functional cross-linking agent or not,
- and an oligonucleotide fixed directly on the functionalised pyrrole, or indirectly on the functionalised pyrrole by means of the cross-linking agent bound with the pyrrole.

The present invention's other advantages and characteristics will be seen more clearly upon reading the following description, which is naturally given as an illustration and is not restrictive, with reference to the appended figures.

EXAMPLES

Example 1

Production of a biochip particularly composed of oligonucleotides grafted onto a conductive polymer according a first embodiment of the present invention.

According to this first embodiment, particularly relating to step a) of the method according to the invention, a gold layer is deposited on a silicon insert so as to form a working electrode for the electropolymerisation of a pyrrole and functionalised pyrrole copolymer. Said gold layer is deposited using a conventional vacuum evaporation or cathodic pulverisation technique. It has a thickness of approximately 1000 to 5000 Å and forms the collective working electrode.

A photosensitive resin is deposited on the gold electrode and a photolithography step makes it possible to make openings in the resin so as to form microtroughs comprising the working electrode in their base, said microtroughs may be addressed simultaneously.

The resin used is preferentially:

a) a positive type photosensitive resin (Novolaque+ diezonaphthoquinone developing in alkaline medium);

b) a Polyimide type negative photosensitive resin (OLIN) developing in an organic solvent;

c) or a polymer engraved by dry or wet engraving.

The microtroughs formed are 100×100×30 $\mu$m in size.

The resin is deposited on the gold electrode using a conventional spinning centrifugation technique. A structured substrate according to step a) of the method according to the present invention is obtained in this way.

The collective electropolymerisation step b) is carried out using a pyrrole and functionalised pyrrole solution.

In this example, the functionalised pyrrole is N-ethylaminepyrrole and the solution used for electropolymerisation is an aqueous/ethanol or acetonitrile solution comprising 0.1 mole of pyrrole, and a functionalised pyrrole/pyrrole molar ratio of 5% to 0.5% by weight of functionalised pyrrole. This solution is hereafter referred to as an electrolytic bath.

The method to obtain the functionalised pyrrole monomer with an $NH_2$ function is easy and is described for example in I. Jurkowsky, R. Baudy, Synthesis 1981, p. 481.

The electropolymerisation is carried out by immersion in the electrolytic bath of the structured substrate obtained above, with suitable electrochemical reagents. These reagents are for example electrolytic salts ($Li^+ClO_4^-$, quaternary ammonium salts, Li-toxylate, or lithium, potassium or sodium sulphonate polystyrene).

The solvents for electropolymerisation are, for example, $Ca_3CN$, water, ethanol and water-ethanol mixtures. The pyrrole contained in the bath shows a concentration of the order of $10^{-1}$ to $10^{-3}$ M/l.

A platinum counter-electrode and a calomel reference electrode are immersed in the electrolytic bath and are independent of the silicon insert, only the working electrode is incorporated in the insert structure.

A layer of pyrrole and functionalised pyrrole copolymer is thus formed and deposited only on the base of the microtroughs by electrodeposition.

Figure 1:
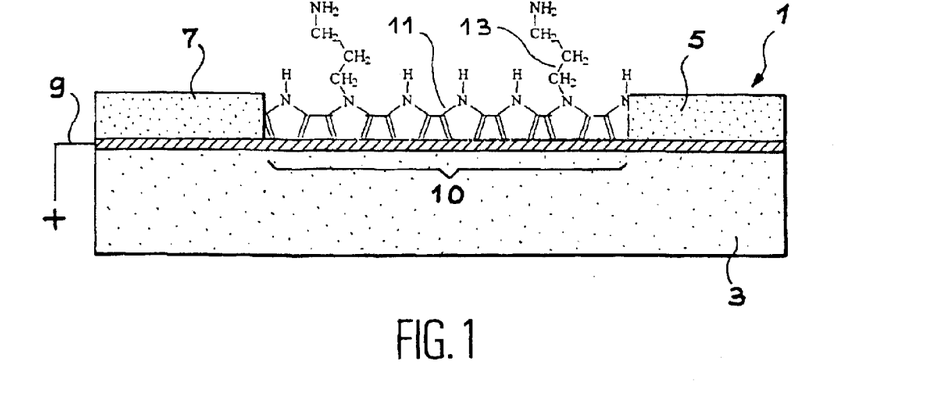
FIG. 1 is a diagram of a section view of a structured substrate according to a first embodiment of steps a) and b) of the method according to the present invention.

FIG. 1 is a diagram of a section view of a substrate obtained according to this first embodiment of the method according to the present invention. In this figure, reference 1 relates to the structured substrate formed in this example, composed of a silicon insert 3, a gold layer 5 and a photosensitive resin layer 7. Reference 9 relates to the connection of the gold layer with an electric current generator for electropolymerisation, reference 10 to a microtrough, and references 11 and 13 relates to the pyrrole (reference 11) and N-ethylamine pyrrole (reference 13) copolymer formed by electrodeposition on the gold layer 5 at the base of the microtrough 10.

In this example, the biological molecule fixation step c) is an indirect fixation step. It comprises the fixation of a cross-linking agent on the $NH_2$ function of the N-ethylamine pyrrole electrodeposited on the base of the microtroughs.

The cross-linking agent used in this example is succinimidyl 4-(p-maleimidophenyl) butyrate) SMPB described above.

This fixation is carried out by forming a covalent bond between the $NH_2$ function of the functionalised pyrrole and the succinate function of the SMPB.

It is carried out by immersing the previously formed substrate in a $10^{-3}M$ SMPB solution in a solvent (dimethylformamide).

The polypyrrole formed is insoluble in this solution and in the majority of standard solvents.

Figure 2:
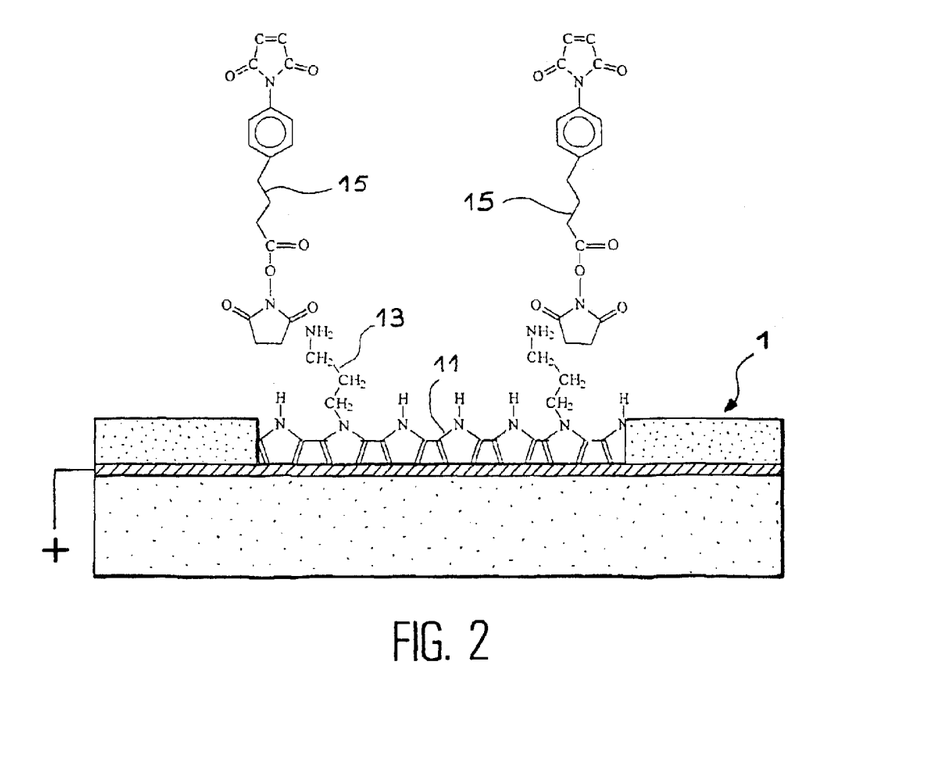
FIG. 2 is a diagram of a section view of a structured substrate according to the embodiment represented in FIG. 1, and also comprising a cross-linking agent for indirect fixation of a biological molecule.

FIG. 2 is a diagram of a section view of the structured substrate obtained in this way. In this diagram, reference 1 relates to the structured substrate represented in FIG. 1, and reference 15 relates to the cross-linking agent SMPB. This FIG. 2 also demonstrates the reaction between the succinimide group of the cross-linking agent and the amine function of the pyrrole.

Therefore, in this example microtroughs coated with a polypyrrole comprising a surface functionalisation, by means of SMBP, of maleimide type reagent groups were produced.

These SMBP maleimide groups enable the fixation of the biological probe on the previously electrodeposited polypyrrole film.

The biological probe used in this example is a mixture of functionalised oligonucleotides with an SH thiol group.

The oligonucleotides were prepared with a conventional automated synthesis and functionalised with a thiol group. The functionalised oligonucleotides are taken up by micropipetting in microwells and injected into microtroughs by means of a dispensing microrobot.

Figure 3:
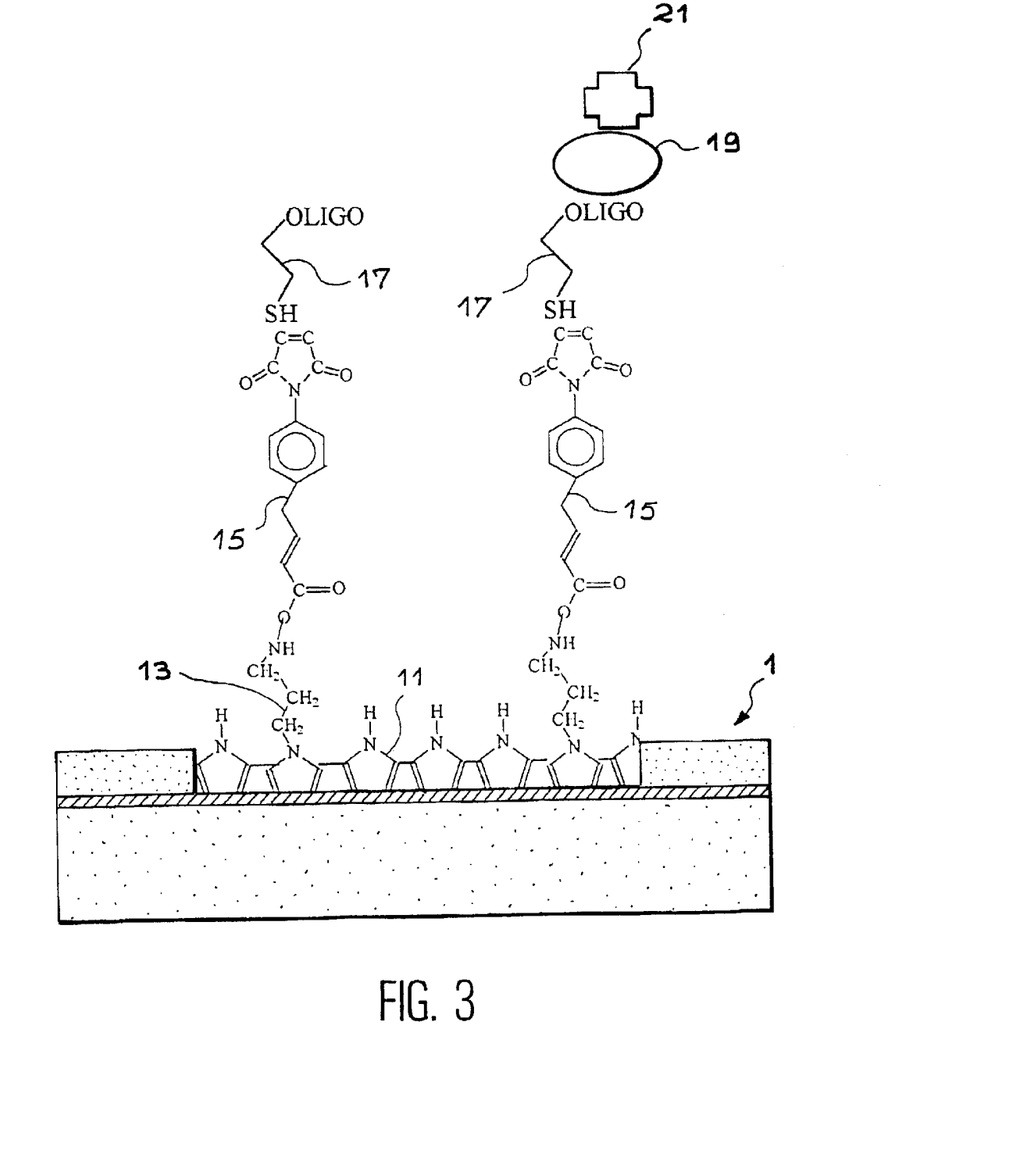
FIG. 3 is a diagram of a section view of a structured substrate represented in FIG. 2, illustrating the indirect fixation of an oligonucleotide on the cross-linking agent.

FIG. 3 is a diagram of a section view of the structured substrate represented in FIG. 2, illustrating the fixation of the oligonucleotide on the cross-linking agent. In this figure, reference 1 relates to the structured substrate formed in this example, references 11 and 13, as in FIGS. 1 and 2, relate to the pyrrole and N-ethylamine pyrrole copolymer, reference 15 to the cross-linking agent SMBP represented in FIG. 2 and reference 17 relates to an oligonucleotide. This FIG. 3 also demonstrates the reaction between the maleimide function of the cross-linking agent and the —SH oligonucleotide.

The probe density was analysed by fixation of oligonucleotides labelled with a biotin (reference 19 in FIG. 3) and using recognition with streptavidine Cy3 (reference 21 in FIG. 3).

The analysis was carried out using a conventional fluorescence detection method, applied to the biotin/streptavidine pair.

Example 2

Production of a biochip particularly composed of oligonucleotide probes grafted onto a conductive polymer according to a second embodiment of the method according to the present invention.

According to this second embodiment, particularly relating to step a) of the method according to the invention, a negative photosensitive resin is deposited on a silicon insert coated with a natural $SiO_2$ film.

As in example 1, microtroughs are then formed by photolithography such that the base of the microtroughs, hereafter referred to as sites, are composed of the silicon oxide layer.

The sites are then functionalised by silanisation: said functionalisation is a collective step of the method according to the invention, it is carried out by immersing the silicon insert comprising previously formed microtroughs in a functionalised silanisation agent with a pyrrole in a suitable solvent. The silanisation agent is N-(3-(trimethyoxysilyl) propyl) pyrrole, and the solvent is an ethanol/water (95/5) mixture or toluene.

On the base of the microtroughs, or sites, a monolayer of silane comprising a regular alignment of pyrrole sites, is obtained.

This monolayer is capable of initiating and promoting the adhesion of a polypyrrole film by electropolymerisation: it forms a working electrode for the collective electropolymerisation of the method according to the present invention.

Electropolymerisation on such a monolayer is for example described in the article by P. Simon et al., J. Am. Chem. Soc. 1982, 104, 2031.

The next step is step b) of the method according to the invention, the electropolymerisation of a pyrrole and N-ethylamine pyrrole copolymer hereafter referred to as Py and Py-R-F, where R and F are respectively a spacer group and a reactive chemical function.

The functionalised silicon insert with silane pyrrole in fact forms the anode of an electrolytic cell. It is immersed in a suitable electrolytic bath, containing both polymers, a counter-electrode and a reference electrode.

The electrolytic bath also comprises Py and Py-R-F of the $Li^+$ electrolytic salts in a water/ethanol or acetonitrile solvent.

The counter-electrode is a platinum electrode. During the electropolymerisation, the pyrrole and substituted pyrrole nuclei are inserted in and bound with the pyrrole units of the silane monolayer.

Figure 4:
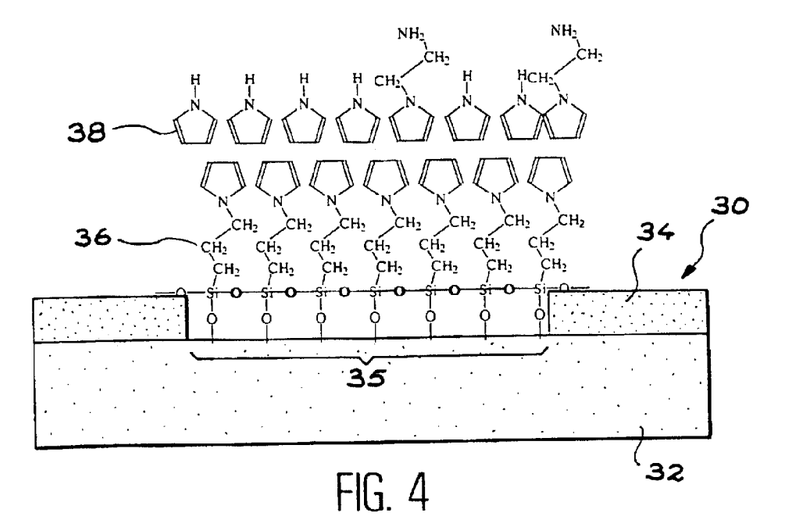
FIG. 4 is a diagram of a section view of a structured substrate according to a second embodiment of the method according to the present invention.

FIG. 4 appended illustrates the product obtained in this way and also shows the formation of covalent bonds between the different pyrrole cycles.

In this figure, reference 32 relates to the silicon insert, reference 34 to the photosensitive resin layer, reference 35 to a microtrough, reference 36 to the silane monolayer, and reference 38 to the layer of pyrrole and functionalised pyrrole copolymer.

The biochip is produced as in example 1:

reactions with the bi-functional cross-linking agent: collective step, immobilisation of the functionalised oligonucleotide probes with a thiol group (—S—H) by mechanical addressing with a robot by GESIM type liquid jet printing (piezoelectric head) or with a BROWN type robot.

Example 3

Production of a biochip particularly composed of oligonucleotide probes grafted onto a conductive polymer according to a third embodiment of the method according to the present invention.

In this example of an embodiment of the method according to the present invention, the microtroughs were produced by photolithography of a resin deposited on a gold electrode on the surface of a silica insert as in example 1 above.

Thiolisation of the gold layer at the base of the microtroughs was then performed by a functionalised pyrrole with an —SH group according to the following formula:

The reaction was carried out by immersing the above-mentioned insert in a solution containing the functionalised pyrrole with a thiol in a solvent such as dimethylformamide DMH for example.

The thiol adhered on the gold at the base of the microtroughs to form a pyrrole monolayer. The combined gold layer and pyrrole fixed on said layer form a working electrode for the collective electropolymerisation of step b) of the method according to the invention. In fact, the specimen serves as an anode for the collective priming of the electropolymerisation.

Steps b) and b) of the method according to the invention were then carried out as in examples 1 and 2 above.

Figure 5:
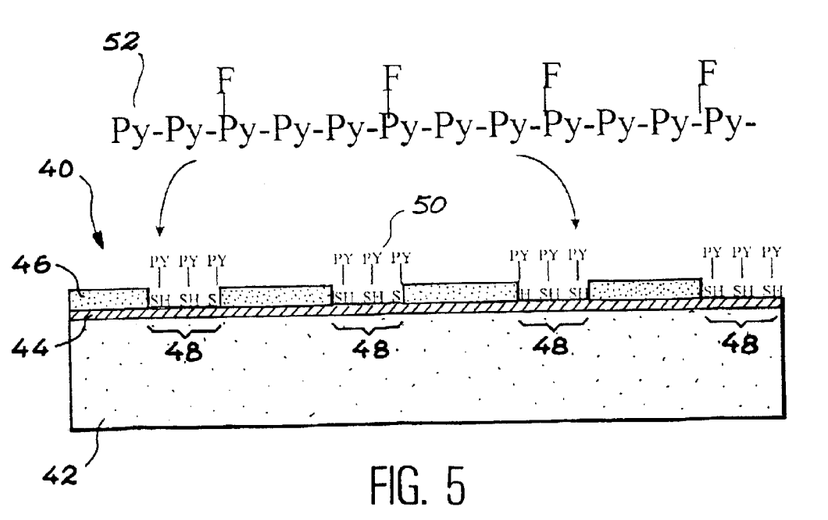
FIG. 5 is a diagram of a section view of a structured substrate according to a third embodiment of steps a) and b) of the method according to the present invention.

FIG. 5 appended is a diagram illustrating the product obtained in this example. It consists of a section view of a structured substrate 40 comprising a silicon insert 42, a gold layer 44, a photosensitive resin layer 46 wherein microtroughs 48 are formed, a pyrrole monolayer 50 adhered onto the gold at the base of the microtroughs, and a film 53 of pyrrole Py and functionalised pyrrole copolymer. In this figure, the curved arrows indicate the electrodeposition of the above-mentioned film on the functionalised pyrrole 50 adhered by thiol groups onto the gold at the base of the microtroughs.

Example 4

Additional Examples

Another approach consists of using a deposition of functionalised polypyrrole, such as:

either an oligonucleotide immobilisation support, or a support to start in situ oligonucleotide synthesis.

This technique makes it possible to replace advantageously a silanisation step wherein a monolayer is more difficult to produce, by a polymer film comprising a well-controlled thickness and number of functional sites.

To do this, films of a copolymer comprising a given proportion of functionalised pyrrole with reference to the pyrrole is produced by electropolymerisation. These polypyrrole films, deposited on a gold electrode, instead of silicon or glass, show a parasite fluorescence of an intensity well below that observed with the other substrates.

The functionalisation may be carried out:

1. on the nitrogen of the pyrrole by an $NH_2$ or epoxy function, for example:

These functions may serve both for the immobilisation of the probes and the in situ synthesis;

2. in position 1, 2 or 3 of the pyrrole by an oxyamine (R—$ONH_2$) or carbonyl (R, R'C=0 where preferentially R'=$CH_3$) function. In this case, these functions serve only for probe immobilisation. The oligonucleotide preferentially comprises either a carbonyl function or an oxyamine function according to the substrate. The oxyamine-carbonyl coupling reaction offers the advantage of being very rapid and results in immobilisation times of less than 10 minutes, compared to a few hours as in the previous case;

3. on the nitrogen of the pyrrole by a nucleotide preferentially comprising a T base. This functionalised serves for the immobilisation of probes comprising a psolarene group in 5'. This group reacts under the effect of light at 365 nm to perform a cycloaddition between the double bond of the psolarene and the double bond 5,6 of Thymine; the reaction time is relatively short: approximately 15 min.

What is claimed is:

1. A method of producing a blank biochip, comprising:
   a) providing a substrate;
   b) depositing a layer of material onto a surface of said substrate;
   c) coating the layer of material with a resin layer; and
   d) producing a plurality of microwells in the resin layer wherein the layer of material forms at least a part of the base of the microwells; and
   e) initiating and promoting on said base of the microwells the adhesion of a copolymer film comprising pyrrole and functionalized pyrrole by electropolymerization after the formation of the microwells,
   wherein the copolymer film allows for the fixation of a biological probe on the base of the microwells.

2. The method of claim 1, further comprising
   e) directly or indirectly fixating a biological probe to the functionalised pyrrole by injecting a biological probe solution, in one or more microwells in the presence of chemical reagents required for the fixating.

3. The method of claim 1, wherein the layer of material is a metallic layer and wherein b) further comprises
   depositing the metallic layer onto the substrate; depositing a layer of resin or polymer onto the metallic layer; and engraving the resin layer to form microwells; and wherein the metallic layer forms at least a part of the base of the microwells.

4. The method of claim 3, wherein the metallic layer is a gold layer.

5. The method of claim 4, which further comprises
   chemically treating the gold layer at the base of the microwells in the presence of a functionalized pyrrole to form a pyrrole monolayer to the gold layer at the base of the microwells.

6. The method of claim 5, wherein the functionalized pyrrole contains a thiol group.

7. The method of claim 6, wherein the functionalized pyrrole with a thiol group has the following chemical formula:

wherein n is from 2 to 10.

8. The method according to claim 1, wherein the substrate is a silicon insert.

9. The method of claim 1, wherein the substrate is a silicon insert and the layer of material is a layer of silane comprising an alignment of pyrrole sites; wherein the method further comprises depositing a layer of resin on the silicon insert, which is coated with an $SiO_2$ film; and engraving the resin layer to form the microwells, wherein the $SiO_2$ film forms at least a part of the base of the microwells; and treating the microwells with a functionalized silanization agent and a pyrrole to fix the silane layer comprising an alignment of pyrrole sites on the $SiO_2$ film in the base of the microwells.

10. The method of claim 9, wherein the silanisation agent is selected from the group consisting of N(3-(trimethoxysilyl)propyl)pyrrole, a functionalized pyrrole with a —$SiCl_3$, and a functionalized pyrrole with a —Si(OMe)$_3$ group.

11. The method of claim 1, which further comprises
immersing the structured substrate in an electrolytic bath comprising a solution of pyrrole, functionalised pyrrole, and suitable chemical reagents for electropolymerisation, in the presence of a counterelectrode which is immersed in the electrolytic bath and is independent of the structured substrate, wherein the layer of material forms a working electrode.

12. The method of claim 1, wherein the functionalised pyrrole is a pyrrole with a group selected from the group consisting of an $NH_2$ group, a thiol group, an N-hydroxysuccinimide ester group, a trimethoxy silyl group, a carboxyl group, an aldehyde group, and an isothiocyanate group.

13. The method of claim 1, wherein the functionalised pyrrole is selected from the group consisting of:

14. The method of claim 2, wherein prior to fixating the biological probe, the method further comprises collectively fixating a cross-linking agent on the functionalized pyrrole in the presence of suitable chemical reagents, wherein the crosslinking agent comprises a first function enabling its fixation onto the functionalised pyrrole, and a second function enabling the fixation of the biological probe on the cross-linking agent.

15. The method of claim 14, wherein the cross-linking agent is selected from the group consisting of a dialdehyde, a diisothiocyanate, a diacid, a succinic anhydride, and a derivative thereof.

16. The method of claim 14, wherein the cross-linking agent selected from the group consisting of:

17. The method of claim 2, wherein the biological probe is selected from the group consisting of an oligonucleotide, DNA, RNA, a peptide, a glucide, a lipid, a protein, an antibody, and an antigen.

18. The method of claim 17, wherein the oligonucleotide is functionalized with a thiol group.

19. The method according to claim 4, which further comprises
chemically treating the gold layer at the base of the microwells in the presence of a functionalised pyrrole to form a monolayer of pyrrole on the gold layer at the base of the microwells.

20. The method of claim 19, wherein the pyrrole is functionalized with a thiol group.

21. The method of claim 20, wherein the functionalized pyrrole with a thiol group has the following chemical formula:

wherein n is from 2 to 10.

22. The method of claim 2, wherein the substrate is a silicon insert.

23. The method of claim 2, which further comprises
immersing the structured substrate in an electrolytic bath comprising a solution of pyrrole, functionalized pyrrole, and suitable chemical reagents for electropolymerisation, in the presence of a counterelectrode which is immersed in the electrolytic bath and is independent of the structured substrate, wherein the layer of material forms a working electrode.

24. The method according to claim 2, wherein the functionalised pyrrole is a pyrrole comprising a group consisting of an $NH_2$ group, a thiol group, an N-hydroxysuccinimide ester group, a trimethoxy silyl group, a carboxyl group, an aldehyde group, and a isothiocyanate group.

25. The method according to claim 2, wherein the functionalised pyrrole is selected from the group consisting of:

26. A blank biochip comprising in this order: a substrate; a layer of material that can initiate and promote the adhesion of a pyrrole and functionalised pyrrole copolymer film on the layer of material by electropolymerisation; a layer of resin coating the layer of material, forming microwells such that the base of the microwells is composed at least partly of the layer of material; and a pyrrole and functionalised pyrrole copolymer layer fixed on the base of the microwells.

27. A biochip comprising in this order; a silica substrate; a gold layer comprising pyrrole sites; a resin layer coating the gold layer comprising pyrrole sites forming microwells such that the base of the microwells is composed at least partly of the gold layer comprising pyrrole sites; a pyrrole and functionalised pyrrole copolymer layer fixed on the gold layer comprising pyrrole sites at the base of the microwells, wherein the functionalised pyrrole is bound or not bound to a bi-functional cross-linking agent, and an oligonucleotide fixed directly on the functionalised pyrrole or fixed indirectly on the functionalised pyrrole by the cross-linking agent bound to the pyrrole.

28. The method of claim 2, wherein the biological probe is a functionalized oligonucleotide and which is fixed directly or indirectly onto the functionalized pyrrole.

29. A biochip comprising in this order; a silica substrate; a silane layer comprising pyrrole sites; a resin layer coating the silane layer comprising pyrrole sites forming microwells such that the base of the microwells is composed at least partly of the silane layer comprising pyrrole sites; a pyrrole and functionalised pyrrole copolymer layer fixed on the silane layer comprising pyrrole sites at the base of the microwells, wherein the functionalised pyrrole is bound or not bound to a bi-functional cross-linking agent, and an oligonucleotide fixed directly on the functionalised pyrrole or fixed indirectly on the functionalised pyrrole by the cross-linking agent bound to the pyrrole.

* * * * *

UNITED STATES PATENT AND TRADEMARK OFFICE
CERTIFICATE OF CORRECTION

PATENT NO. : 6,803,228 B1
DATED : October 12, 2004
INVENTOR(S) : Caillat et al.

It is certified that error appears in the above-identified patent and that said Letters Patent is hereby corrected as shown below:

Title page,
Item [73], Assignee, should read:
-- [73] Assignee: Commissariat A L'Energie Atomique, Paris (FR) --

Signed and Sealed this

Eighteenth Day of January, 2005

JON W. DUDAS
*Director of the United States Patent and Trademark Office*